(12) United States Patent
Vollmers et al.

(10) Patent No.: US 7,611,894 B2
(45) Date of Patent: Nov. 3, 2009

(54) ANTI-IDIOTYPE ANTIBODIES OF THE HUMAN MONOCLONAL ANTIBODY SC-1, AND THEIR PRODUCTION AND USE

(75) Inventors: Heinz Peter Vollmers, Würzburg (DE); Hans Konrad Müller-Hermelink, Würzburg (DE)

(73) Assignee: Debiovision, Montreal, Quebec (CA)

( * ) Notice: Subject to any disclaimer, the term of this patent is extended or adjusted under 35 U.S.C. 154(b) by 0 days.

(21) Appl. No.: 10/579,147

(22) PCT Filed: Nov. 15, 2004

(86) PCT No.: PCT/IB2004/004407

§ 371 (c)(1), (2), (4) Date: Mar. 19, 2007

(87) PCT Pub. No.: WO2005/047456

PCT Pub. Date: May 26, 2005

(65) Prior Publication Data

US 2007/0269425 A1    Nov. 22, 2007

(30) Foreign Application Priority Data

Nov. 13, 2003  (DE) ................ 103 52 977

(51) Int. Cl.
*C12N 5/12*  (2006.01)
(52) U.S. Cl. .................... 435/326; 434/130.1
(58) Field of Classification Search .............. None
See application file for complete search history.

(56) References Cited

U.S. PATENT DOCUMENTS

2005/0032131 A1   2/2005  Wolozin et al.

FOREIGN PATENT DOCUMENTS

EP      0 376 746 A2   7/1990

OTHER PUBLICATIONS

Essani et al. (J of Clinical Investigation, vol. 76, 1985, pp. 1649-1656).*
Brandlein, Stephanie et al. "Natural IgM Antibodies and Immunosurveillance Mechanisms Against Epithelial Cancer Cells in Humans." *Cancer Research*. Anonymous pp. 7995-8005, 2003.
Essani, Karim et al. "Anti-Idiotypic Antibodies Against a Human Multiple Organ-Reactive Autoantibody Detection of Idiotopes in Normal Individuals and Patients with Autoimmune Diseases." (Oct. 1985) 76: 1649-56.
H3 Pharma Inc. International Search Report for PCT/IB2004/004407, Mar. 26, 2006.
H3 Pharma Inc. Written Opinion of the International Searching Authority for PCTIB/2004/004407, May 13, 2006.
Herlyn, D., et al. "Anti-Idiotypic Antibodies Bear the Internal Image of a Human Tumor Antigen." *Science* (1986) 232: 100-2.
Playfair, J.H.L. et al. "Selected Pages." *Immunology at a Glance*. ,8th Ed.,10, pp. 26,40, 41 and 45, Blackwell Publishing, 2005.
Vollmers, H. Peter et al. "Adjuvant Therapy for Gastric Adenocarcinoma with the Apoptosis-Inducing Human Monoclonal Antibody SC-1: First Clinical and Histopathological Results." *Oncology Reports*, pp. 549-552, 1998.
Vollmers, H. Peter et al. "Tumor-Specific Apoptosis Induced by the Human Monoclonal Antibody SC-1: A New Therapeutical Approach for Stomach Cancer." *Oncology Reports*, pp. 35-40, 1998.
Vollmers, H. Peter et al. "SC-1, a Functional Human Monoclonal Antibody Against Autologous Stomach Carcinoma Cells." *Cancer Research*, pp. 2471-2476, 1989.
Xu, J. L., et al. "Diversity in the CDR3 Region of V(H) is Sufficient for most Antibody Specificities." *Immunity* (2000) 13: 37-45.

* cited by examiner

*Primary Examiner*—Larry R. Helms
*Assistant Examiner*—Meera Natarajan
(74) *Attorney, Agent, or Firm*—Clark & Elbing LLP; Kristina Bieker-Brady; Jan N. Tittel

(57) ABSTRACT

The invention features anti-idiotype antibodies of the human monoclonal antibody SC-1, as well as methods for producing and using the anti-idiotype antibodies.

6 Claims, 2 Drawing Sheets

SC-1 heavy chain sequence

```
                                                                                       CDR I
          AGG TCC CTG AGA CTC TCC TGT GCA GCC TCT GGA TTC ACC TTC AGT  AGC TAT GGC ATG CAC  TGG GTC CGC CAG GCT CCA  (SEQ ID NO:4)
DP-49     Arg Ser Leu Arg Leu Ser Cys Ala Ala Ser Gly Phe Thr Phe Ser  Ser Tyr Gly Met His  Trp Val Arg Gln Ala Pro  (SEQ ID NO:3)
20/11     --- --- --- --- --- --- --- --- --- --- --- --- --- --- ---  -C- --- --- --- ---  --- --- --- --- --- ---  (SEQ ID NO:2)
                                                                       Thr                                            (SEQ ID NO:1)

CDR II
          GGC AAG GGG CTG GAG TGG GTG GCA  GTT ATA TCA TAT GAT GGA AGT AAT AAA TAC TAT GCA GAC TCC GTG AAG GGC  CGA  (SEQ ID NO:4)
DP-49     Gly Lys Gly Leu Glu Trp Val Ala  Val Ile Ser Tyr Asp Gly Ser Asn Lys Tyr Tyr Ala Asp Ser Val Lys Gly  Arg  (SEQ ID NO:3)
20/11     --- --- --- --- --- --- --- ---  --- T-- --- --- --- --- --- --- --- --- --- --- --- --- --- --- ---  ---  (SEQ ID NO:2)
                                               Leu                                                                    (SEQ ID NO:1)

TTC ACC ATC TCC AGA GAC AAT TCC AAG AAC ACG CTG TAT CTG CAA ATG AAC AGC CTG AGA GCT GAG GAC ACG GCT GTG TAT TAC  (SEQ ID NO:4)
DP-49     Phe Thr Ile Ser Arg Asp Asn Ser Lys Asn Thr Leu Tyr Leu Gln Met Asn Ser Leu Arg Ala Glu Asp Thr Ala Val Tyr Tyr  (SEQ ID NO:3)
20/11     --- --- --- --- --- --- --- --- --- --- --- -T- G-- --- --- --- --- --- --- --G A-- --- --- -C--- --T          (SEQ ID NO:2)
                                                        Met Val                                 Thr             Ala          (SEQ ID NO:1)

CDR III                                                                                        JH6b
          TGT GCG ############################################### #################################################************  (SEQ ID NO:4)
DP-49     Cys Ala ############################################### #################################################************  (SEQ ID NO:3)
          ---     AGA GAT GTC TCC CCA ACT CGG TGG GTT GAC TGG AGC GTT GAC TGG GGT ATG TAC TAC TAC TAC TAC GGT ATG GAC GTC TGG GGC CAG GGA ACT CTG GTC  (SEQ ID NO:2)
                  Arg Asp Val Ser Pro Thr Arg Trp Val Asp Trp Ser Val Asp Trp Gly Met Tyr Tyr Tyr Tyr Tyr Gly Met Asp Val Trp Gly Gln Gly Thr Leu Val  (SEQ ID NO:1)
                   DK5a
```

FIGURE 3

SEQUENCE LISTING

<160> NUMBER OF SEQ ID NOS: 4

<210> SEQ ID NO 1
<211> LENGTH: 108
<212> TYPE: PRT
<213> ORGANISM: Homo sapiens

<400> SEQUENCE: 1

```
Arg Ser Leu Arg Leu Ser Cys Ala Ala Ser Gly Phe Thr Phe Ser Thr
1               5                   10                  15

Tyr Gly Met His Trp Val Arg Gln Ala Pro Gly Lys Gly Leu Glu Trp
            20                  25                  30

Val Ala Val Leu Ser Tyr Asp Gly Ser Asn Lys Tyr Tyr Ala Asp Ser
        35                  40                  45

Val Lys Gly Arg Phe Thr Ile Ser Arg Asp Asn Ser Lys Asn Met Val
    50                  55                  60

Tyr Leu Gln Met Asn Ser Leu Arg Thr Glu Asp Thr Ala Ala Tyr Tyr
65                  70                  75                  80

Cys Ala Arg Asp Val Ser Pro Thr Arg Trp Val Ser Asp Tyr Tyr Tyr
                85                  90                  95
```

```
Tyr Gly Met Asp Val Trp Gly Gln Gly Thr Leu Val
            100                 105

<210> SEQ ID NO 2
<211> LENGTH: 324
<212> TYPE: DNA
<213> ORGANISM: Homo sapiens

<400> SEQUENCE: 2
aggtccctga gactctcctg tgcagcctct ggattcacct tcagtaccta tggcatgcac      60
tgggtccgcc aggctccagg caaggggctg gagtgggtgg cagttttatc atatgatgga     120
agtaataaat actatgcaga ctccgtgaag ggccgattca ccatctccag agacaattcc     180
aagaacatgg tgtatctgca aatgaacagc ctgaggactg aggacacggc tgcgtatttc     240
tgtgcgagag atgtctcccc aactcggtgg gttagcgact actattacta cggtatggac     300
gtctggggcc agggcactct ggtc                                            324

<210> SEQ ID NO 3
<211> LENGTH: 82
<212> TYPE: PRT
<213> ORGANISM: Homo sapiens

<400> SEQUENCE: 3

Arg Ser Leu Arg Leu Ser Cys Ala Ala Ser Gly Phe Thr Phe Ser Ser
1               5                   10                  15

Tyr Gly Met His Trp Val Arg Gln Ala Pro Gly Lys Gly Leu Glu Trp
            20                  25                  30

Val Ala Val Ile Ser Tyr Asp Gly Ser Asn Lys Tyr Tyr Ala Asp Ser
        35                  40                  45

Val Lys Gly Arg Phe Thr Ile Ser Arg Asp Asn Ser Lys Asn Thr Leu
    50                  55                  60

Tyr Leu Gln Met Asn Ser Leu Arg Ala Glu Asp Thr Ala Val Tyr Tyr
65                  70                  75                  80

Cys Ala

<210> SEQ ID NO 4
<211> LENGTH: 246
<212> TYPE: DNA
<213> ORGANISM: Homo sapiens

<400> SEQUENCE: 4
aggtccctga gactctcctg tgcagcctct ggattcacct tcagtagcta tggcatgcac      60
tgggtccgcc aggctccagg caaggggctg gagtgggtgg cagttatatc atatgatgga     120
agtaataaat actatgcaga ctccgtgaag ggccgattca ccatctccag agacaattcc     180
aagaacacgc tgtatctgca aatgaacagc ctgagagctg aggacacggc tgtgtattac     240
tgtgcg                                                                246
```

ANTI-IDIOTYPE ANTIBODIES OF THE HUMAN MONOCLONAL ANTIBODY SC-1, AND THEIR PRODUCTION AND USE

CROSS-REFERENCE TO RELATED APPLICATIONS

This application is the U.S. National Stage of International PCT Application No. PCT/IB2004/004407, filed Nov. 15, 2004, which claims benefit of German Patent Application No. DE 10352977.2, filed Nov. 13, 2003, each of which is hereby incorporated by reference.

BACKGROUND OF THE INVENTION

The present invention is related to the field of cancer diagnosis and treatment and, more specifically, to polypeptides, such as anti-idiotype antibodies, useful in the diagnosis, detection, monitoring, and treatment of neoplasms in a mammal, e.g., a human.

The use of human monoclonal antibodies in diagnosing and treating cancer has great therapeutic potential. Antibodies can prevent further growth of cancer cells and can influence control mechanisms of the cancer cells and thereby initiate the events that lead to apoptosis. The production of human monoclonal antibodies used therapeutically is based on the initial isolation of antibodies that are a component of the cancer patient's immune response. With the production of hybridomas, it is possible to obtain the antibodies in large quantities and above all, in monoclonal form.

Given the therapeutic potential of human monoclonal antibodies, there is a need for agents that can be used to detect the presence of such antibodies in a sample or in a patient.

SUMMARY OF THE INVENTION

We have generated an anti-idiotype antibody that specifically binds the human monoclonal IgM antibody SC-1. As SC-1 is a tumor-specific antibody and induces apoptosis in stomach adenocarcinoma cells and not in healthy tissue, the SC-1 anti-idiotype antibody provides an excellent diagnostic tool for detecting the presence of an SC-1 antibody in a patient and also can be used as a control antigen in conjunction with a variety of therapeutic and diagnostic methods. The technique used to generate the SC-1 anti-idiotype antibody can also be used to generate anti-idiotype antibodies against other therapeutic human monoclonal IgM antibodies. Moreover, as the SC-1 anti-idiotype antibody mimics the antigen recognized by the SC-1 antibody, this anti-idiotype antibody can be used to generate a tumor-specific immune response in a patient.

Accordingly, the first aspect of the invention features an isolated anti-idiotype antibody that specifically binds a polypeptide including the SC-1 monoclonal antibody heavy chain sequence set forth in FIG. 3 (SEQ ID NO:1). In a desirable embodiment of this aspect of the invention, the anti-idiotype antibody specifically binds CD 5 positive B lymphocytes.

The second aspect of the invention features the hybridoma cell line with DSMZ (Deutsche Sammlung von Mikroorganismen und Zellkulturen GmbH) accession number DSM ACC2625, and in the third aspect the invention features the anti-idiotype antibody expressed by the hybridoma cell line having DSMZ accession number DSM ACC2625. In desirable embodiments of the third aspect of the invention, the anti-idiotype antibody includes a detectable agent. In another desirable aspect, the invention features a humanized antibody having the binding specificity of the anti-idiotype antibody expressed by the hybridoma cell line having DSMZ accession number DSM ACC2625. The humanized antibody desirably includes a detectable agent.

In the fourth aspect, the invention features a method of generating an immune response in a mammal against the anti-idiotype antibody expressed by the cell line having DSMZ accession number DSM ACC2625. This method involves immunizing a mammal with the purified anti-idiotype antibody in a pharmaceutically acceptable carrier. Desirably, the anti-idiotype antibody is humanized prior to immunizing the mammal, e.g., a human. In other desirable embodiments of the fourth aspect of the invention, the mammal is a non-human mammal, e.g., a sheep, a goat, a horse, a rabbit or a rodent, for example, a mouse or a rat. In further desirable embodiments immunizing the mammal results in cells in the mammal expressing polypeptides, for example, antibodies, that specifically bind to the anti-idiotype antibody. The cells expressing the polypeptides may also be isolated from the mammal and fused to myeloma cells to generate an antibody-expressing hybridoma cell. Moreover, the hybridoma cell may be tested to determine if it expresses an antibody that specifically binds the anti-idiotype antibody expressed by the cell line having DSMZ accession number DSM ACC2625.

In the fifth aspect, the invention features a method for producing an anti-idiotype antibody in a non-human mammal, for instance, a sheep, a goat, a horse, a rabbit or a rodent, for example, a mouse (e.g., a BALB/C mouse) or a rat. This method involves, (i) immunizing a non-human mammal with a purified human monoclonal IgM antibody, for example, by means of intraperitoneal injection, (ii) isolating a B lymphocyte from the non-human mammal, (iii) contacting a non-human myeloma cell from the same species as the non-human mammal with the isolated B lymphocyte under conditions that lead to fusion of the myeloma cell and the B lymphocyte to yield a non-human hybridoma cell, (iv) culturing the non-human hybridoma cell, (v) determining whether the non-human hybridoma cell expresses an antibody, and (vi) determining whether the antibody expressed by the non-human hybridoma cell specifically binds the human hybridoma cell or the human monoclonal IgM antibody expressed by the human hybridoma cell. In a desirable embodiment, the purified human monoclonal IgM antibody used in this method includes the SC-1 monoclonal antibody heavy chain sequence of SEQ ID NO:1 as shown in FIG. 3.

In other desirable embodiments of the fifth aspect of the invention, the non-human mammal is sacrificed, for example, within four days of the last immunization with the purified human monoclonal IgM antibody. Immunizing in the context of the method of the fifth aspect of the invention desirably involves an immunization regimen.

In additional desirable embodiments of the fifth aspect of the invention, the purified human monoclonal IgM antibody is obtained from the supernatant of cultured human hybridoma cells, where these human hybridoma cells express the human monoclonal IgM antibody, and purifying the human monoclonal IgM antibody from the hybridoma supernatant desirably involves affinity chromatography and/or, ion exchange chromatography and/or gel filtration.

In addition, fusing of non-human B lymphocyte, e.g., a BALB/C mouse B lymphocyte or a rat B lymphocyte, and non-human myeloma cells, e.g., mouse NS-O myeloma cells, or rat myeloma cells, desirably involves use of polyethylene glycol (PEG). Further, whether the non-human hybridoma cell expresses an antibody desirably includes use of an enzyme-linked immunosorbent assay (ELISA), for example, one carried out after 2, 3, 4, or 5 weeks of culturing the non-human hybridoma cell.

Definitions

By an "anti-idiotype antibody" is meant an antibody that specifically binds to the antigen-binding site of another antibody and, therefore, is specifically bound by the other antibody. Desirably the anti-idiotype antibody mimics the epitope normally recognized by another antibody, e.g., a human monoclonal IgM antibody such as SC-1 described in, for example, Vollmers et al. ("Tumor-Specific Apoptosis Induced by the Human Monoclonal Antibody SC-1: A New Therapeutic Approach for Stomach Cancer," Oncology Reports 5:35-40, 1998), or by an antibody containing the sequence of SEQ ID NO:1, or a functional fragment of an antibody containing the sequence of SEQ ID NO:1. In another desirable embodiment, an anti-idiotype antibody is the antibody expressed by the cell line having DSMZ (Deutsche Sammlung von Mikroorganismen und Zellkulturen GmbH) accession number DSM ACC2625. In a further desirable embodiment, the anti-idiotype antibody mimics the tumor-specific glycostructure present on an isoform of CD55 expressed by the human adenocarcinoma cell line 23132 (DSMZ accession number DSM ACC 201), where this CD55 isoform has an approximate molecular weight of 82 kDa in sodium dodecyl sulfate (SDS) polyacrylamide gel electrophoresis (PAGE).

By a "candidate compound" or "test compound" is meant a chemical, be it naturally-occurring or artificially-derived, that is surveyed for its ability to specifically bind an anti-idiotype antibody that is expressed by the cell line having DSMZ accession number DSM ACC2625 or an anti-idiotype antibody that specifically binds an antibody containing the sequence of SEQ ID NO:1, e.g., in one of the assay methods described herein. Candidate or test compounds include, for example, peptides, polypeptides, synthetic organic molecules, naturally-occurring organic molecules, nucleic acid molecules, and components thereof.

By "detectable agent" is meant a compound that is linked to an anti-idiotype antibody to facilitate detection. Such a "detectable agent" may be covalently or non-covalently linked to an anti-idiotype antibody. In addition, the linkage may be direct or indirect. Examples of "detectable agents" include, protein purification tags, cytotoxins, enzymes, paramagnetic labels, enzyme substrates, co-factors, enzymatic inhibitors, dyes, radionuclides, chemiluminescent labels, fluorescent markers, growth inhibitors, cytokines, antibodies, and biotin.

By a "functional fragment," as used herein in reference to polypeptide or an anti-idiotype antibody, is meant a fragment that retains at least one biological activity of the full-length polypeptide. An example of such a biological activity is the ability to specifically bind an antigen. For instance, a functional fragment may specifically bind to a polypeptide containing the SC-1 heavy chain sequence shown in FIG. 3 (SEQ ID NO:1) or to human adenocarcinoma cell line 23132 (DSMZ accession number DSM ACC 201). The biological activities of a functional fragment may be determined, for example, using any one of the assays described herein.

Examples of functional fragments of an antibody are $V_L$, $V_H$, $F_V$, $F_C$, Fab, Fab', or $F(ab')_2$ fragments which are known to one skilled in the art (see, e.g., Huston et al., Cell Biophys. 22:189-224, 1993; and Harlow and Lane, Using Antibodies: A Laboratory Manual, Cold Spring Harbor Laboratory Press, N.Y., 1999). In desirable embodiments, such a fragment includes one or more of the Complement Determining Regions (CDR) of the $V_H$ or the $V_L$ regions of the SC-1 anti-idiotype antibody expressed by the cell line having DSMZ accession number DSM ACC2625.

A "humanized antibody" as used herein, is a genetically engineered antibody in which a minimum of a non-human, e.g., a murine, antibody sequence is combined with human antibody sequence and still maintains the binding specificity of the original non-human antibody. In desirable embodiments, a humanized antibody contains 15%, 20%, 25%, 30%, or 40% non-human sequence. In more desirable embodiments, a humanized antibody contains 5% or 10% non-human sequence. In addition, a humanized antibody desirably induces no or only a minimal human immune response against any non-human sequence remaining in the humanized antibody.

A "hybridoma," as used herein, is any cell that is artificially created by the fusion of a normal cell, such as an activated lymphocyte, with a neoplastic cell, e.g., a myeloma. The hybrid cell, which results from the fusion of at least two cells, may produce a monoclonal antibody or T cell product identical to that produced by the immunologically-competent parent. In addition, these cells, like the neoplastic parent, are immortal.

An "immune response" as used herein, involves activation of the immune system of a mammal to specifically target an antigen. Desirably, this antigen is one that is mimicked by an anti-idiotype antibody. In further desirable embodiments, the antigen is one that is specifically expressed by neoplastic cells and not by non-neoplastic cells. Accordingly, in another desirable embodiment, the antigen contains the tumor-specific glycostructure present on an isoform of CD55 expressed by the human adenocarcinoma cell line 23132 (DSMZ accession number DSM ACC 201), where this CD55 isoform has an approximate molecular weight of 82 kDa in SDS-PAGE.

A "neoplastic cell," as used herein, refers to a cell which is undergoing cell division, not undergoing apoptosis, or both, under inappropriate conditions. For example, a "neoplastic cell" may undergo cell division when a corresponding normal cell does not undergo cell division, or, alternatively, a "neoplastic cell" may not respond to normal cell-cycle checkpoint controls.

A "protein purification tag," as used herein, is a peptide, e.g., an epitope tag, that is covalently or non-covalently added to a protein to aid in the purification of the protein. Desirably such peptides bind with high affinity to an antibody or to another peptide such as biotin or avidin. Commercially available examples of epitope tags include His-tags, HA-tags, FLAG®-tags, and c-Myc-tags. However, any epitope that is recognized by an antibody also may be used as a protein purification tag. See, for example, Ausubel et al., *Current Protocols in Molecular Biology*, Wiley Interscience, New York, 2001; and Sambrook et al., *Molecular Cloning: A Laboratory Manual*, 3$^{rd}$ edition, Cold Spring Harbor Laboratory Press, N.Y., 2001. Protein purification tags may be cleaved from a protein, for example, by using an enzyme, e.g., thrombin, or a chemical, e.g., cyanogen bromide.

By "specifically binds" and "specifically recognizes" as used herein in reference to a polypeptide, e.g., an anti-idiotype antibody, is meant an increased affinity of a polypeptide for a particular protein, e.g., an antigen, relative to an equal amount of any other protein. For example, an anti-idiotype antibody desirably has an affinity for its antigen that is least 2-fold, 5-fold, 10-fold, 30-fold, or 100-fold greater than for an equal amount of any other antigen, including related antigens. Binding of a polypeptide to another polypeptide may be determined as described herein, and by any number of standard methods in the art, e.g., Western analysis, ELISA, or co-immunoprecipitation.

By "substantially identical" is meant a polypeptide or nucleic acid exhibiting at least 80%, 85%, 90%, or 95% identity to a reference amino acid or nucleic acid sequence, or a fragment thereof. In desirable embodiments, the polypeptide or nucleic acid sequence is at least 98%, 99%, 99.4%, 99.5%, 99.6%, 99.7%, 99.8%, 99.9%, or even 100% identical to a reference amino acid or nucleic acid sequence. For polypeptides, the length of comparison sequences will generally be at least 3, 4, 5, 6, 8, 10, or 15 amino acids and desirably at least 20 or 25 contiguous amino acids. In more desirable embodiments, the length of comparison sequences is at least 30, 50, 75, 90, or 95 contiguous amino acids, or even the full-length amino acid sequence. For nucleic acids, the length of comparison sequences will generally be at least 9, 10, 12, 15, 18, 20, 24, or 25 contiguous nucleotides, and desirably at least 30 contiguous nucleotides. In more desirable embodiments, the length of comparison sequences is at least 50, 75, 150, 225, 270, 280, 285, or 290 contiguous nucleotides, or even the full-length nucleotide sequence.

Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Multiple sequences may also be aligned using the Clustal W(1.4) program (produced by Julie D. Thompson and Toby Gibson of the European Molecular Biology Laboratory, Germany and Desmond Higgins of European Bioinformatics Institute, Cambridge, UK) by setting the pairwise alignment mode to "slow," the pairwise alignment parameters to include an open gap penalty of 10.0 and an extend gap penalty of 0.1, as well as setting the similarity matrix to "blosum." In addition, the multiple alignment parameters may include an open gap penalty of 10.0, an extend gap penalty of 0.1, as well as setting the similarity matrix to "blosum," the delay divergent to 40%, and the gap distance to 8.

By "purified" or "isolated" is meant separated from other components that naturally accompany it. Typically, a factor is "purified" or "isolated" when it is at least 50%, by weight, free from proteins, antibodies, and naturally-occurring organic molecules with which it is naturally associated, or in reference to a nucleic acid molecule, is free from the nucleic acid sequences that naturally flank the sequence of the nucleic acid molecule in the genome of an organism. Desirably, the factor is at least 75%, more desirably, at least 90%, and most desirably, at least 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques, such as those described by Ausubel et al. (*Current Protocols in Molecular Biology*, Wiley Interscience, New York, 2001). The factor is desirably at least 2, 5, or 10 times as pure as the starting material, as measured using polyacrylamide gel electrophoresis, column chromatography, optical density, BPLC analysis, or Western analysis (Ausubel et al., *Current Protocols in Molecular Biology*, Wiley Interscience, New York, 2001). Desirable methods of purification include immunoprecipitation, column chromatography such as immunoaffinity chromatography and nickel affinity columns, magnetic bead immunoaffinity purification, and panning with a plate-bound antibody.

An anti-idiotype antibody can serve as a cost-effective tool for detecting the presence of a therapeutic or diagnostic antibody, for example, an SC-1 antibody, in a sample or in biochemical experiments, pharmacological tests, and/or in laboratory diagnosis.

Other features and advantages of the invention will be apparent from the following Detailed Description, the Drawings, and the Claims.

BRIEF DESCRIPTION OF THE DRAWINGS

FIGS. 1C and 1D show the results of immunofluorescence double staining with the anti-SC-1 idiotype antibody and an anti-CD5 antibody. The two cells labeled by the anti-idiotype antibody (FIG. 1C) are also recognized by the anti-CD5 antibody (FIG. 1D).

FIG. 2A is a negative control on autologous spleen tissue, FIG. 2B shows SC-1 anti-idiotype antibody staining on autologous spleen tissue, FIG. 2C shows SC-1 anti-idiotype antibody staining on spleen tissue from a stomach cancer patient whose cancer does not express the antigen recognized by the SC-1 antibody, and FIG. 2D shows SC-1 anti-idiotype antibody staining on spleen tissue from a healthy person.

FIG. 3 shows the amino acid (SEQ ID NO:1) and nucleic acid (SEQ ID NO:2) sequences of the human monoclonal antibody SC-1 variable region heavy chain (labeled 20/11) in comparison to the homologous human Ig germ line H-chain V-region gene DP-49 (SEQ ID NOS:3 and 4). In this figure, "---" indicates that the sequences are the same for SC-1 and DP49, and differences are indicated in the SC-1 sequences by setting forth the particular amino acid or nucleotide differences. "###" and "***" also indicate differences in the sequences. The complement determining regions (CDRs) are marked.

DETAILED DESCRIPTION

Figure 1:
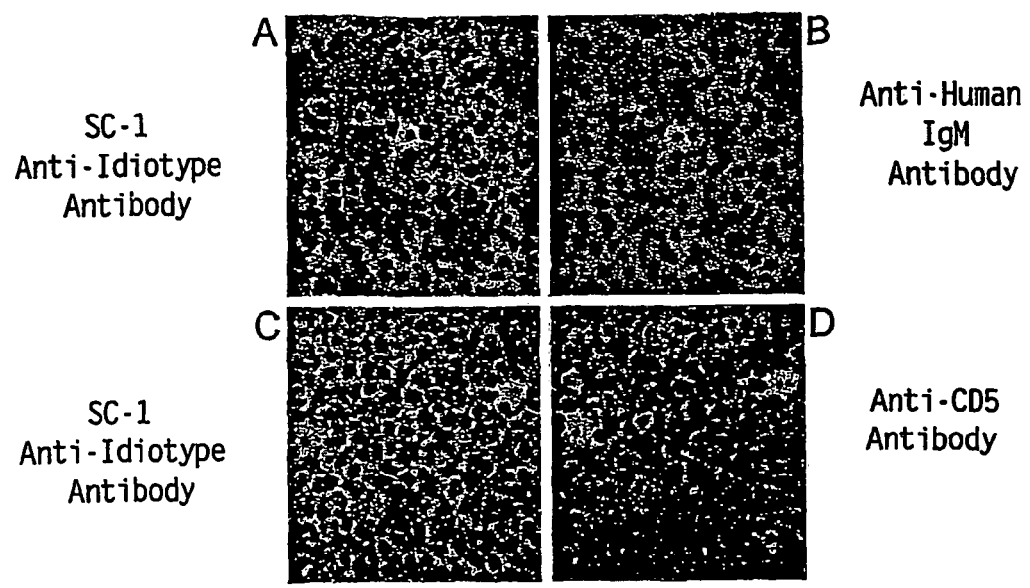
FIGS. 1A to 1D are images showing immunofluorescent double staining. The fluorescing cell is specifically bound by both the anti-idiotype antibody (FIG. 1A) and by the rabbit anti-human IgM antibody (FIG. 1B).

The present invention features anti-idiotype antibodies that can be used in the field of cancer diagnosis and treatment and to generate a tumor-specific immune response in a patient. In addition, the invention features methods of generating anti-idiotype antibodies against human monoclonal IgM antibodies. In particular, we generated an anti-idiotype antibody that specifically binds the SC-1 human monoclonal IgM antibody described, for example, in Vollmers et al. ("Tumor-Specific Apoptosis Induced by the Human Monoclonal Antibody SC-1: A Novel Therapeutical Approach for Stomach Cancer," 5:35-40, 1998). This anti-idiotype antibody, which is expressed by the cell line having DSMZ accession number DSM ACC2625, can be used to generate a tumor-specific immune response in a patient, as well as in a variety of methods for detecting whether a patient expresses an antibody that specifically binds the 82 kDa tumor-specific isoform of CD55 present on cell line 23132 (DSMZ accession number DSM ACC 201) and to screen for compounds that bind the anti-idiotype antibody.

The cell line that produces the SC-1 anti-idiotype antibody (cell line 6/22-10-30-13) was deposited on Nov. 6, 2003 at the German Collection of Microorganisms and Cell Cultures ("DSMZ"—Deutsche Sammlung von Mikroorganismen und Zellkulturen GmbH, Mascheroder Weg 1b, 38124 Braunschweig, Germany) under the terms of the Budapest Treaty and has been assigned DSMZ accession number DSM ACC2625.

Antibodies are immunoglobulin (Ig) molecules that each have two identical light and two identical heavy chains and are connected to each other by disulfide bridges. Each of the chains contains a region of about 110 amino acids with variable sequence, while the rest of each chain has an area with constant sequence. Antibodies are made by B-lymphocytes in a process involving gene rearrangement. During the development of these cells, the genes encoding the variable domains are assembled from genetic elements. In the case of the $V_H$ domains there are three elements, the un-rearranged $V_H$ gene, D segment, and $J_H$ segment. In the case of the $V_L$ domains, there are two elements, the un-rearranged $V_L$ (V Lambda or V Kappa) gene and the $J_L$ (J Lambda or J Kappa) segment. Random combination of these gene segments and random combination of the rearranged $V_H$ and $V_L$ domains generate a large repertoire of antibodies, capable of binding to a large diversity of equally diverse antigens. Further, the $V_H$ and $V_L$ regions each have three hypervariable regions that are also designated Complement Determining Regions (CDR) and four framework regions (FR). The FRs are the backbone of the antibody and the CDRs are the parts of the antibody that bind the antigen. One skilled in the art can determine the FR and CDR regions of an antibody by comparing the amino acid sequence of a number of antibodies raised in the same species (see, e.g., Altschul et al., Nucleic Acids Res. 25:3389-3402, 1997; and Kabat et al., Sequences of Proteins of Immunological Interest, $5^{th}$ edition, NIH Publication No. 91-3242, U.S. Department of Health and Human Services, 1991).

In general monoclonal antibodies are produced by hybridomas that are cellular hybrids obtained by cell fusion of normal lymphocytes with immortal myeloma cells. The hybridoma cells that are generated by the fusion have the properties of both parent cells. Accordingly the hybridoma, like the lymphocyte produces antibodies, and, like the myeloma cell, is immortal. Thus, hybridomas may be used for the production of the antibodies in large quantities (Köhler and Millstein, Nature 256:495, 1975). Each hybrid cell resulting from the fusion produces monoclonal antibodies, the specificity of which is determined by the original lymphocyte cell. The hybridoma cells are cultured and those that produce antibodies of the desired specificity are selected. This process leads to antibodies that specifically bind a particular antigenic determinant, For example, monoclonal antibodies that specifically bind to tumor antigens, are useful for diagnosis and treatment of tumor cells.

A hybridoma may also be produced to generate anti-idiotype antibodies. Production of anti-idiotype antibody expressing hybridoma cells depends on the availability of appropriately immunized B lymphocytes and/or on the availability of the substance used for immunization. This process may include the creation of a suitable myeloma cell as a fusion partner for the B lymphocytes. The individual idiotypes are amino acid sequences that generally are specifically bound by all monoclonal antibodies expressed by a given B lymphocyte.

Production of an Anti-Idiotype Antibody

An idiotype is the genetically determined variation of intramolecular structures in the variable regions of immunoglobulins. The precise genetic basis of idiotype variability has only been partially explained. However, idiotype variation involves the amino acid sequence and protein structure (so-called determinants) especially in the area of the antigen-binding site, also referred to as the idiotope. The term "idiotype" designates the complete set of determinants of a variable region of an antibody molecule.

An anti-idiotype antibody may be generated with a process that uses a purified human monoclonal IgM antibody or a human hybridoma cell line that expresses a human monoclonal IgM antibody. For example a process for generation of an anti-idiotype antibody may involve culturing a human hybridoma cell line that secretes a human monoclonal IgM antibody into its supernatant and purifying this IgM antibody, for example, using affinity chromatography, ion exchange chromatography, gel filtration, or a combination thereof. This purified human monoclonal IgM antibody may then be used to immunize a non-human mammal, such as a mouse or a rat, by means of, for instance, an intraperitoneal injection or in vitro directly on isolated B lymphocytes. B lymphocytes may then be isolated from the non-human mammal sacrificed up to four days after the last immunization, and the isolated B lymphocytes may be brought into contact with myeloma cells of same species (e.g., mouse or rat) under conditions that lead to fusion of the myeloma cells with the B lymphocytes to generate a non-human hybridoma cell. These non-human hybridoma cells can then be cultured and tested (e.g., using ELISA) for expression of idiotype Ig antibodies, e.g., IgM, IgA, or IgG antibodies, after, for example, three weeks of culturing. These Ig antibodies can be tested for specific binding to the human hybridoma cells and to various IgM antibodies, including the human monoclonal IgM antibody used to immunize the non-human mammal.

In this process, the human hybridoma cell that expresses the human monoclonal IgM antibody may be generated by fusing B lymphocytes from a lymphatic organ like the spleen, lymph nodes, or blood of a cancer patient, e.g., a patient with signet ring cell carcinoma of the stomach, with SPM 4-0 heteromyeloma cells. Other exemplary heteromyeloma cell lines that can be used in this process include HAB-1 (Faller, et al., Br. J. Cancer 62:595-598, 1990), CB-F7 (Delvig et al., Hum. Antibodies Hybridomas 6:42-46, 1995), K6H6B5 (Delvig et al., Hum. Antibodies Hybridomas 6:42-46, 1995), H7NS.934 (Delvig et al., Hum. Antibodies Hybridomas 6:42-46, 1995), SHM-D33 (Bron et al., Proc. Natl. Acad. Sci. USA 81:3214-3217, 1984), and B6B11 (Borisova et al., Vopr. Virusol. 44:172-174, 1999).

To generate an anti-idiotype antibody of the SC-1 human monoclonal IgM antibody, the human hybridoma cells used in the process would need to express the human monoclonal SC-1 antibody or a functional fragment thereof, e.g., a $V_L$, $V_H$, Fv, Fc, Fab, Fab' and F(ab')$_2$ fragment. The amino acid sequence of the human homoclonal SC-1 antibody variable region heavy chain is found in the following publication: (Vollmers et al., "Tumor-Specific Apoptosis Induced by the Human Monoclonal Antibody SC-1: A New Therapeutical Approach for Stomach Cancer," Oncology Reports 5: 35-40, 1998) and is that of SEQ ID NO:1.

In particular, to obtain murine anti-idiotype SC-1 antibodies, BALB/C mice were immunized with purified human monoclonal SC-1 antibody. B lymphocytes obtained from these mice were fused with NS/O myeloma cells in polyethylene glycol (PEG)-1500 using electrostimulation (with the use of a fusion generator).

Tumor Vaccine

To generate an immune response in a patient, for example, a tumor-specific immune response, an anti-idiotype antibody, or a fragment thereof, may be administered by any suitable means that results in an immune response in the patient. The polypeptide may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, or intraperitoneal) administration route. The pharmaceutical compositions may be formulated according to conventional pharmaceutical practice (see, e.g., Remington: The Science and Practice of Pharmacy (20th ed.), ed. A. R. Gennaro, Lippincott, Williams & Wilkins, 2000 and Encyclopedia of Pharmaceutical Technology, eds. J. Swarbrick and J. C. Boylan, 1988-1999, Marcel Dekker, New York).

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found, for example, in Remington (The Science and Practice of Pharmacy (20th ed.), ed. A. R. Gennaro, Lippincott, Williams & Wilkins, 2000 and Encyclopedia of Pharmaceutical Technology, eds. J. Swarbrick and J. C. Boylan, 1988-1999, Marcel Dekker, New York).

It is not intended that the administration of an anti-idiotype antibody to a patient to generate an immune response be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to generate an immune response. The anti-idiotype antibody may be administered to the patient in a single dose or in multiple doses. When multiple doses are administered, the doses may be separated from one another by, for example, one day, two days, one week, two weeks, or one month. For example, the anti-idiotype antibody, e.g., the antibody expressed by the cell line having DSMZ accession number DSM ACC2625 may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. The precise dose will vary dependent on the anti-idiotype antibody used, and, for example, when generating a tumor-specific immune response, the density, on the tumor surface, of the antigen which the anti-idiotype antibody mimics, and the rate of clearance of the anti-idiotype antibody. For example, the dosage of the anti-idiotype antibody can be increased if the lower dose does not induce a sufficient immune response. Conversely, the dosage of the anti-idiotype antibody can be decreased if the neoplasm is cleared from the patient.

While the attending physician ultimately will decide the appropriate amount and immunization and dosage regimen, an effective amount of an anti-idiotype antibody for inducing an immune response, may be, for example, in the range of about 0.1 mg to 50 mg/kg body weight/day or 0.70 mg to 350 mg/kg body weight/week. Desirably the effective amount is in the range of about 0.50 mg to 20.0 mg/kg, and more desirably in the range of about 0.50 mg to 15.0 mg/kg, for example, about 0.2, 0.3, 0.5, 1.0, 1.5, 2.0, 2.5, 3.0, 3.5, 4.0, 4.5, 5.0, 5.5, 6.0, 7.0, 8.0, 8.5, 9.0, 10.0, 11.0, 12.0, 13.0, 14.0, or 15.0 mg/kg body weight administered daily, every other day, or twice a week. Suitable dose sizes will vary with the size of the patient, but will typically range from about 0.1 mL to about 5 mL.

In Vitro Diagnostic Assays

The anti-idiotype antibodies of the present invention may be used in a variety of diagnostic assays to determine whether a subject expresses an antibody or an antigen that specifically binds the anti-idiotype antibody. For example, the diagnosis of neoplasms can involve a binding agent to detect polypeptide markers in a sample. See, e.g., Harlow and Lane, Using Antibodies: A Laboratory Manual, Cold Spring Harbor Laboratory Press, N.Y., 1999. As an anti-idiotype antibody can mimic an antigen expressed by a neoplastic cell and not by a non-neoplastic cell, the anti-idiotype antibody may, for example, be used as a control antigen for enzyme-linked immunosorbent assay (ELISA), Western blotting, or in situ detection of tumor cells in a tissue sample. Moreover, one skilled in the art may use an anti-idiotype antibody may be used to determine whether a patient expresses an antibody that specifically binds to the anti-idiotype antibody. For example, an anti-idiotype antibody may be used to detect the presence of an SC-1 antibody in blood obtained from an individual. The presence of the SC-1 antibody may be indicative of the individual having stomach adenocarcinoma. Other assays in which an anti-idiotype antibody of the invention may be used include, immunohistochemical staining and fluorescence activated cell sorting (FACS). Furthermore the anti-idiotype antibodies of the present invention can be used to identify CD-5 positive B lymphocytes.

An ELISA assay typically involves the use of a polypeptide, such as an anti-idiotype antibody, immobilized on a solid support to bind to a biological sample, e.g., one containing antibodies from a cancer patient. If antibodies from the biological sample bind the anti-idiotype antibody, the bound antibodies may then be detected using a detection reagent that contains a reporter group and that specifically binds to the antibody/anti-idiotype antibody complex. Such detection reagents include, for example, any binding agent that specifically binds to an antibody, such as an anti-immunoglobulin, protein G, protein A, or a lectin. Alternatively, a competitive assay may be utilized, in which an antibody that specifically binds the anti-idiotype antibody is labeled with a reporter group and allowed to bind to the immobilized anti-idiotype antibody after incubation of the anti-idiotype antibody with the biological sample. The extent to which components of the sample inhibit the binding of the labeled antibody to the anti-idiotype antibody is indicative of the reactivity of a component of the sample with the immobilized anti-idiotype antibody antibody.

The method employed for detecting the reporter group depends upon the nature of the reporter group. For radioactive groups, scintillation counting or autoradiographic methods may be used. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a defined period of time), followed by spectroscopic or other analysis of the reaction products.

Test Extracts and Compounds

In general, an anti-idiotype antibody, e.g., the antibody expressed by the cell line having DSMZ accession number DSM ACC2625 may also be used in high throughput screening techniques to identify compounds that have binding characteristics similar to those of a therapeutic antibody, e.g., an antibody containing the amino acid sequence of SEQ ID NO:1. Such compounds can identified from large libraries of both natural products, synthetic (or semi-synthetic) extracts or chemical libraries, according to methods known in the art.

Those skilled in the art will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from, for example, Brandon Associates (Merrimack, N.H.) and Aldrich Chemical (Milwaukee, Wis.).

Alternatively, libraries of natural compounds in the form of bacterial, fungal, plant, and animal extracts are commercially available from a number of sources, including, but not limited to, Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art (e.g., by combinatorial chemistry methods or standard extraction and fractionation methods). Furthermore, if desired, any library or compound may be readily modified using standard chemical, physical, or biochemical methods.

In addition, those skilled in the art readily understand that methods for dereplication (e.g., taxonomic dereplication, biological dereplication, and chemical dereplication, or any combination thereof) or the elimination of replicates or repeats of materials already known for their effects on compounds associated with estrogen regulation should be employed whenever possible.

When a crude extract is found to bind an anti-idiotype antibody, e.g., the one expressed by the cell line having DSMZ accession number DSM ACC2625, further fractionation of the positive lead extract is necessary to isolate chemical constituents responsible for the observed effect. Thus, the goal of the extraction, fractionation, and purification process is the careful characterization and identification of a chemical entity within the crude extract that binds the anti-idiotype antibody. Methods of fractionation and purification of heterogenous extracts are known in the art.

The following examples are provided for the purpose of illustrating the invention and should not be construed as limiting.

EXAMPLE 1

Materials and Methods

ELISA (Enzyme-Linked Immunosorbent Assay)

ELISA assays were carried out as follows.

Coat the ELISA plate with the primary antibody (10 µg/ml purified SC-1 antibody diluted in phosphate buffered saline (PBS)), add 50 µl of the primary antibody to each well, cover the ELISA plate and store over night at 4° C. On the following day, wash the ELISA plate twice with PBS, add 100 µl RPMI-1640 cell culture medium (with 10% Fetal Calf Serum (FCS)) per well and let stand 1 h at room temperature (RT). Then wash the ELISA plate twice with PBS/0.05% Tween, add 50 µl RPMI-1640 cell culture medium as negative control (2 wells, double determination), pipette 50 µl of the samples (2 wells, double determination) next to each other, and incubate 1 h in the incubation chamber. After the incubation, wash 2 times with PBS, wash twice with PBS/0.05% Tween, wash twice with PBS, pipette 50 µl of the secondary antibody (peroxidase conjugated) (peroxidase conjugated rabbit anti-mouse Ig 1:2000 in PBS/Tween) into each well, and incubate 1 h in incubation chamber. After this incubation, wash twice with PBS, wash once with PBS/0.05% Tween, wash twice with PBS, and wash twice with citrate buffer. For evaluation: dissolve ortho-phenylene-diamine (OPD) tablet (Dako, Hamburg) in citrate buffer with $H_2O_2$ (3 ml citrate buffer+one tablet+5 µl $H_2O_2$), pipette 50 µl stain into each well, and upon positive reaction (yellow coloring), stop with 10 µl 3 M $H_2SO_4$.

Immunoperoxidase Staining

Immunoperoxidase staining was carried out as follows.

The cryopreserved tissue was cut into 4 µm slices and the slide was allowed to dry at least 2 h after cutting. The slide was placed in acetone for 10 min and then dried for 30 min, washed 3 times with Tris/NaCl, incubated for 5 min in Tris, blocked for 15-30 min. with 100 µl 5% milk powder in PBS, and immersed in Tris/NaCl. 100 µl of the respective primary antibody (e.g., anti-idiotype antibody (hybridoma supernatant, undiluted); for the negative control: RPMI-1640/10% FCS; and for the positive control:antibody CK8 diluted 1:50 with bovine serum albumin (BSA)/PBS or antibody CAM 5.2 diluted 1:10 with BSA/PBS (BSA 0.5% in PBS)) were added and incubated for 30 min, and washed 3 times with Tris-NaCl. 100 µl of the respective secondary antibody (e.g., peroxidase-conjugated rabbit anti-mouse Ig in 70% PBS with 30% human serum and 1:50 diluted antibody) were then added, incubated for 30 min, and washed 3 times with Tris/NaCl. The slide was then placed in PBS for 10 min. One diaminobenzidine (DAB) tablet (Sigma, Munich) and one $H_2O_2$ tablet were dissolved in 1 ml tap water. 100 µl of the DAB substrate were pipetted onto the slide, incubated for 10 min, and rinsed with distilled $H_2O$. The place slide was placed in hematoxylin for 5 min, placed under running water for 15 min, and then placed in distilled $H_2O$ and covered with glycerol-gelatin.

Immunohistochemical Fluorescence Double Staining

The indirect immunofluorescence method was used to detect various antigens on one preparation. 4 µm thick sections of cryopreserved human lymphatic tissue were fixed for 10 min with acetone. The staining was carried out in two steps. In the first step, the cryosections were each coated 30 min with a murine anti-idiotype antibody as the primary antibody and a FITC-conjugated rabbit anti-mouse antibody (diluted 1:40 in PBS, pH 7.3) as the secondary antibody. A 60-minute incubation with an unconjugated rabbit anti-mouse antibody (diluted 1:50 in PBS, pH 7.3) followed to saturate the free binding sites of the first antibody. In the second step, Pan-B lymphocyte (diluted 1:50 in PBS, pH 7.3), mouse anti-CD5 (diluted 1:50 in PBS, pH 7.3) or mouse anti-human IgM (diluted 1:100 in PBS, pH 7.3), as the primary antibody, and a TRITC-conjugated rabbit anti-mouse antibody (diluted 1:20 in PBS, pH 7.3), as the secondary antibody, were pipetted onto the cryosections. After each incubation step, the preparations were washed 15 min with PBS, pH 7.3. The preparations were evaluated with a fluorescence microscope.

EXAMPLE 2

Generation and Characterization of an SC-1 Anti-Idiotype Antibody

In the experiment shown by FIG. 1, the immunological origin of the slightly mutated, non-affinity-matured antibody SC-1 was characterized by the generation of a murine monoclonal anti-SC-1 idiotype antibody. By immunizing BALB/C mice with affinity-purified SC-1 antibody and subsequent immortalization of the spleen lymphocytes, it was possible to obtain a monoclonal IgG1 mouse antibody, which reacts exclusively with the SC-1 IgM. A detailed ELISA analysis with different IgM antibodies, including ones that are commercially available, gave no indication of cross reaction with other immunoglobulins. By using immunohistochemical double staining with the anti-idiotype antibody and an anti-CD5 antibody, it was possible to show that both cells that are recognized by the anti-idiotype antibody involve CD 5 positive B lymphocytes (FIGS. 1C and 1D).

Figure 2:
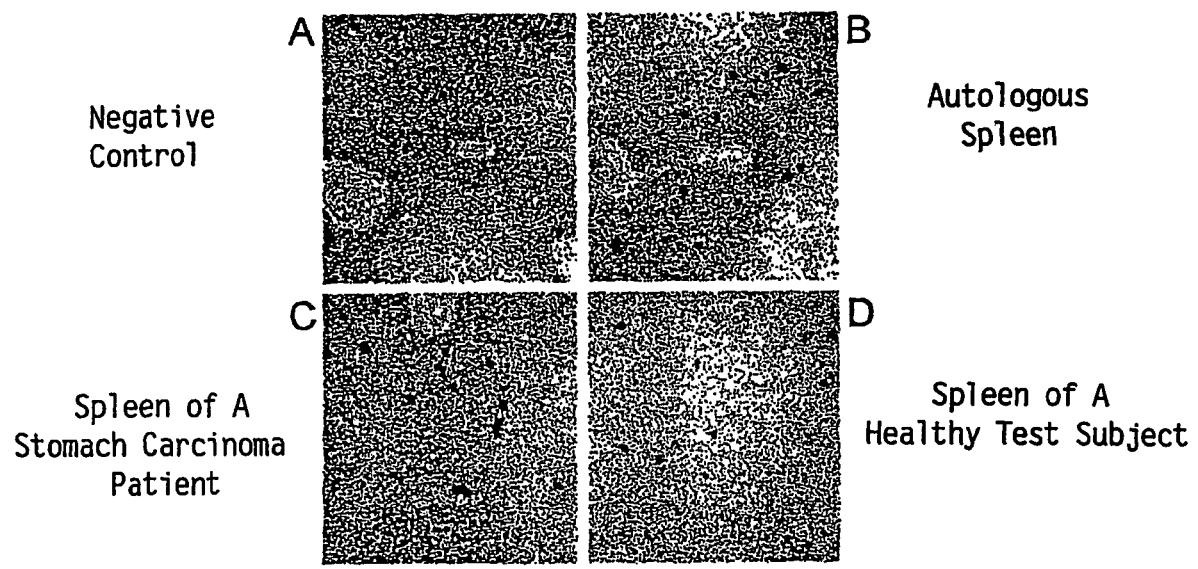
FIGS. 2A to 2D show images of immunoperoxidase staining for analysis of the expression of the anti-idiotype antibody on lymphatic tissue.

The results shown in FIG. 2 indicate that autologous spleen tissue obtained from the stomach cancer patient from whom cells expressing the SC-1 IgM antibody were isolated (FIG. 2B), spleen tissue from an stomach cancer patient whose cancer does not express the antigen recognized by the SC-1 antibody (FIG. 2C), and spleen tissue of a healthy test subject (FIG. 2D), express the idiotype. These immunohistochemical tests show that the SC-1 idiotype is expressed not only in lymphatic organs of cancer patients, but also in healthy test subjects. Thus, SC-1 involves an antibody that is secreted by the cells of the innate immune system in the scope of the first line of defense.

EXAMPLE 3

Use of an SC-1 Anti-Idiotype Antibody as an Anti-Cancer Vaccine

The SC-1 anti-idiotype antibody expressed by the cell line having DSMZ accession number DSM ACC2625 can be used either alone to induce a tumor-specific immune response in patients with a stomach carcinoma or in conjunction with other treatments such as chemotherapy or surgical removal of the stomach carcinoma. The patients are immunized with increasing doses of a purified SC-1 anti-idiotype antibody, desirably a humanized antibody, for 2 months, with additional booster doses during the period of 5 months to 2 years. These patients are regularly assayed throughout the treatment period for an immune response against the SC-1 anti-idiotype antibody, as well as for the disappearance of the stomach carcinoma.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

German patent application number 103 52 977.2, filed Nov. 13, 2004, and all references cited herein are hereby incorporated by reference.

What is claimed is:

1. The hybridoma cell line with DSMZ accession number DSM ACC2625.

2. The anti-idiotype antibody expressed by the hybridoma cell line of claim 1.

3. A humanized antibody having the binding specificity of the anti-idiotype antibody of claim 2.

4. The anti-idiotype antibody of claim 2, wherein said anti-idiotype antibody further comprises a detectable agent.

5. A humanized anti-idiotype antibody having the 6 CDRs of the anti-idiotype antibody expressed by the hybridoma cell line with DSMZ accession number DSM ACC2625, wherein the humanized anti-idiotype antibody specifically binds a polypeptide comprising the SC-1 human monoclonal antibody heavy-chain sequence set forth in SEQ ID NO:1.

6. The humanized anti-idiotype antibody of claim 5, wherein said antibody further comprises a detectable agent.

* * * * *